(12) United States Patent
Bates

(10) Patent No.: US 8,377,032 B2
(45) Date of Patent: Feb. 19, 2013

(54) SYSTEMS AND METHODS FOR ATRAUMATIC IMPLANTATION OF BIO-ACTIVE AGENTS

(75) Inventor: Mark C. Bates, Charleston, WV (US)

(73) Assignee: Nexeon MedSystems, Inc., Encinitas, CA (US)

( * ) Notice: Subject to any disclaimer, the term of this patent is extended or adjusted under 35 U.S.C. 154(b) by 0 days.

(21) Appl. No.: 12/637,701

(22) Filed: Dec. 14, 2009

(65) Prior Publication Data
US 2010/0331814 A1 Dec. 30, 2010

Related U.S. Application Data

(62) Division of application No. 10/894,810, filed on Jul. 19, 2004, now Pat. No. 7,632,262.

(51) Int. Cl.
*A61M 25/06* (2006.01)
*A61M 31/00* (2006.01)

(52) U.S. Cl. .............. 604/506; 604/57; 604/59; 604/60; 604/522; 606/1; 606/167

(58) Field of Classification Search .................. 604/500, 604/502, 506–508, 164.01, 164.12, 170.02, 604/188, 264, 272, 528–530, 532, 891.1, 604/522, 57, 59–60; 606/1, 167
See application file for complete search history.

(56) References Cited

U.S. PATENT DOCUMENTS

| | | | |
|---|---|---|---|
| 3,880,163 A | 4/1975 | Ritterskamp | |
| 4,067,334 A | 1/1978 | Haller | |
| 4,108,177 A | 8/1978 | Pistor | |
| 4,676,781 A | 6/1987 | Phillips | |
| 4,710,162 A * | 12/1987 | Johnson | ........................ 604/506 |
| 4,950,233 A | 8/1990 | Abramowitz | |
| 5,244,460 A | 9/1993 | Unger | |
| 5,273,532 A | 12/1993 | Niezink et al. | |
| 5,284,479 A * | 2/1994 | de Jong | ........................ 604/60 |
| 5,419,777 A | 5/1995 | Hofling | |
| 5,531,780 A | 7/1996 | Vachon | |
| 5,562,613 A * | 10/1996 | Kaldany | ........................ 604/57 |

(Continued)

FOREIGN PATENT DOCUMENTS

| | | |
|---|---|---|
| JP | 9-509865 | 10/1997 |
| JP | 2004-26761 | 1/2004 |

(Continued)

OTHER PUBLICATIONS

PCT International Search Report for PCT/US05/25469, 3 pages (mailed Oct. 3, 2006).

(Continued)

*Primary Examiner* — Quynh-Nhu H Vu
(74) *Attorney, Agent, or Firm* — Foley & Lardner LLP; Nicola A. Pisano

(57) ABSTRACT

Methods and apparatus are provided for delivering a bioactive agent in a needle track formed in a target tissue mass, following formation of the needle track, by avoiding impingement of the agent against target tissue at high velocity or by using capillary action to draw the bioactive agent out of the needle during needle withdrawal. The apparatus comprises a catheter and a needle disposed within the catheter and configured to be selectively extended into the tissue mass to a predetermined depth, while dispensing the agent simultaneously with retraction of the needle along the needle track. Alternatively, or in addition, the needle may be configured to create a tissue space surrounding a distal or lateral surface of the needle, into which the bioactive agent to be infused.

20 Claims, 10 Drawing Sheets

U.S. PATENT DOCUMENTS

| | | | |
|---|---|---|---|
| 5,655,548 | A | 8/1997 | Nelson |
| 5,695,463 | A * | 12/1997 | Cherif-Cheikh ................ 604/60 |
| 5,730,741 | A * | 3/1998 | Horzewski et al. ................ 606/1 |
| 5,860,739 | A | 1/1999 | Cannon |
| 5,910,150 | A | 6/1999 | Saadat |
| 5,941,893 | A | 8/1999 | Saadat |
| 6,024,120 | A * | 2/2000 | Yam et al. ..................... 137/495 |
| 6,051,008 | A | 4/2000 | Saadat |
| 6,102,887 | A | 8/2000 | Altman |
| 6,120,520 | A * | 9/2000 | Saadat et al. .................. 606/170 |
| 6,159,196 | A | 12/2000 | Ruiz |
| 6,264,637 | B1 | 7/2001 | Hogan |
| 6,302,870 | B1 | 10/2001 | Jacobsen |
| 6,346,099 | B1 | 2/2002 | Altman |
| 6,432,119 | B1 * | 8/2002 | Saadat .......................... 606/170 |
| 6,450,937 | B1 * | 9/2002 | Mercereau et al. ................ 600/7 |
| 6,544,236 | B1 | 4/2003 | Cragg |
| 7,316,692 | B2 | 1/2008 | Huffmaster |
| 7,338,471 | B2 | 3/2008 | Bates |
| 7,632,262 | B2 | 12/2009 | Bates |
| 7,686,799 | B2 * | 3/2010 | Leonhardt et al. ............ 604/507 |
| 2002/0049414 | A1 | 4/2002 | Nobles |
| 2003/0191449 | A1 | 10/2003 | Nash |
| 2004/0092892 | A1 | 5/2004 | Kagan |
| 2005/0124999 | A1 | 6/2005 | Teitelbaum |
| 2005/0256361 | A1 | 11/2005 | Mathieu et al. |
| 2005/0261633 | A1 | 11/2005 | Khalaj |
| 2008/0154201 | A1 | 6/2008 | Bates |

FOREIGN PATENT DOCUMENTS

| | | |
|---|---|---|
| WO | WO 95/26776 | 10/1995 |

OTHER PUBLICATIONS

PCT International Search Report for PCT/US05/25470, 2 pages (mailed Sep. 21, 2006).

USPTO Office Action (non-final) for U.S. Appl. No. 10/977,594, 6 pages (mailed Dec. 15, 2006).

USPTO Office Action (final) for U.S. Appl. No. 10/977,594, 6 pages (mailed Jun. 1, 2007).

USPTO Notice of Allowance and Notice of Allowability for U.S. Appl. No. 10/977,594, 7 pages (mailed Oct. 9, 2007).

USPTO Office Action (non-final) for U.S. Appl. No. 10/894,810, 6 pages (mailed Jan. 17, 2007).

USPTO Office Action (final) for U.S. Appl. No. 10/894,810, 8 pages (mailed Aug. 28, 2007).

USPTO Office Action (non-final) for U.S. Appl. No. 10/894,810, 9 pages (mailed Jul. 25, 2008).

USPTO Office Action (final) for U.S. Appl. No. 10/894,810, 8 pages (mailed Feb. 24, 2009).

USPTO Notice of Allowance for U.S. Appl. No. 10/894,810, 6 pages (mailed Aug. 6, 2009).

USPTO Office Action (non-final) for U.S. Appl. No. 12/041,561, 10 pages (mailed Jun. 22, 2009).

Bonan, Raoul, "Local Drug Delivery for the Treatment of Thrombus and Restenosis," J. Invasive Cardiol., 8 (8): 399-402 (Oct. 1996).

Mack, Charles A., et al., "Biologic Bypass with the Use of Adenovirus-Medicated Gene Transfer of the Complementary Deoxyribonucleic Acid for Vascular Endothelial Growth Factor 121 Improves Myocardial Perfusion and Function in the Ischemic Porcine Heart," J. Thorac. Cardiovasc. Surg.. 115 (1): 168-76 (Jan. 1998).

Sanborn, Timothy A., et al., "Percutaneous Endocardial Gene Therapy: In Vivo Gene Transfer and Expression," J. Am. Coll. Card., 33 (2 Suppl.): 262A (Feb. 1999).

Thompson, Craig A., et al., "Percutaneous Transvenous Cellular Cardiomyoplasty," J. Am. Coll. Card., 41 (11): 1964-1971 (Jun. 2003).

Uchida, Yangisawa-Miwa A., et al., "Angiogenic Therapy of Acute Myocardial Infarction by Intrapericardial Injection of Basic Fibroblast Growth Factor and Herapin Sulfate: An Experimental Study," Am. Heart J., 130 (6): 1182-88 (Dec. 1995).

* cited by examiner

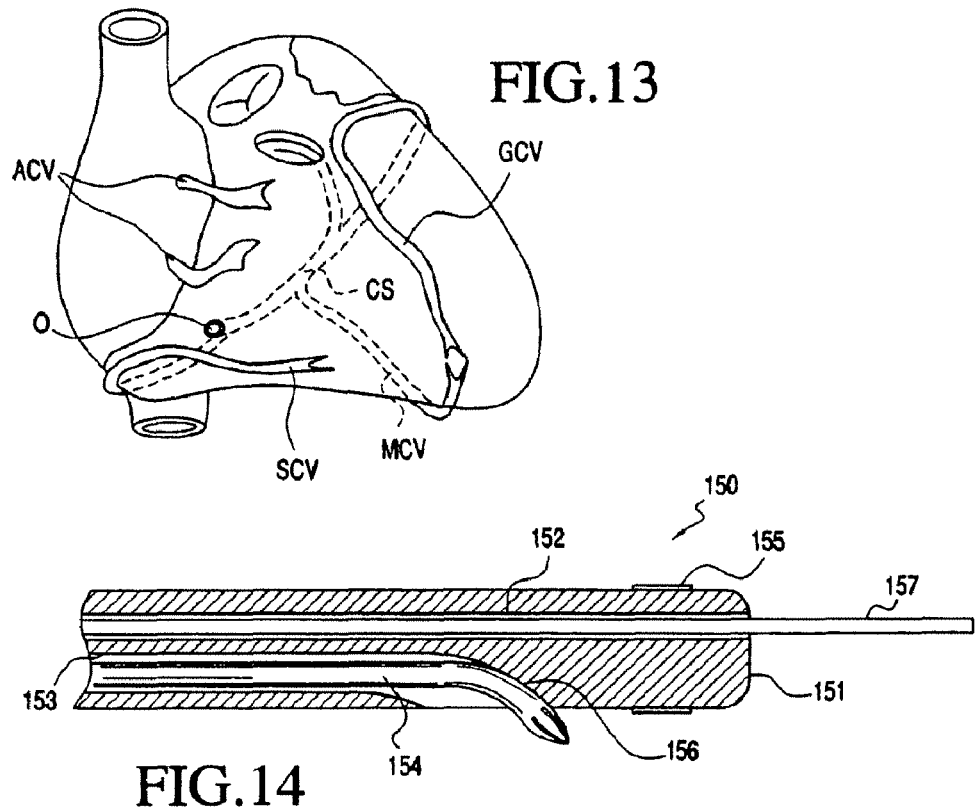
FIG. 13
FIG. 14
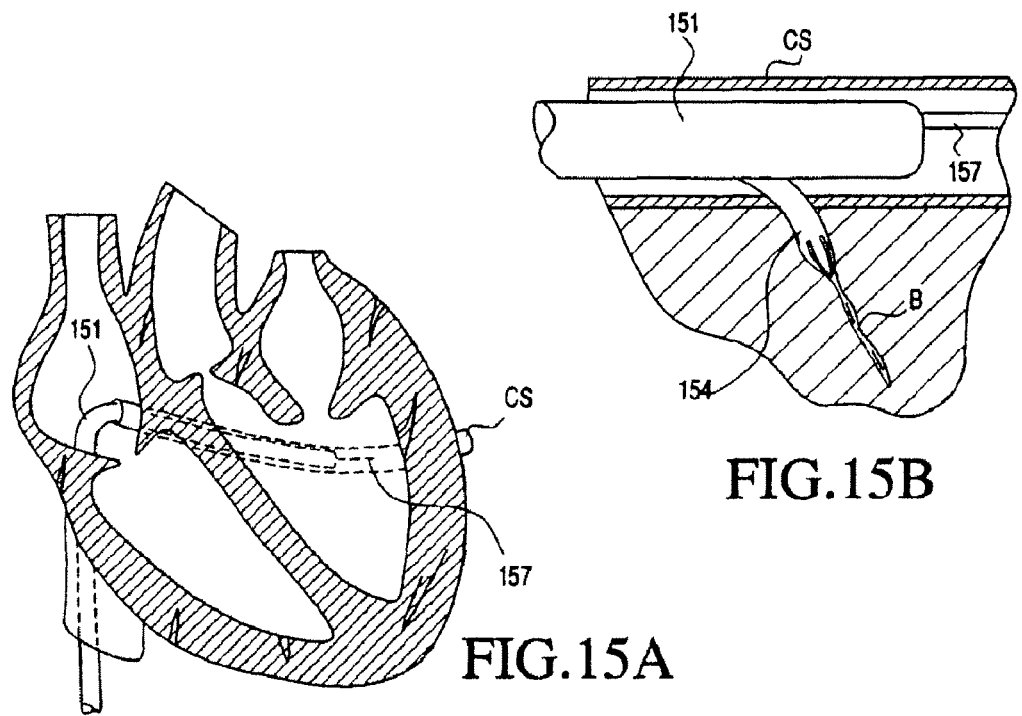
FIG. 15A
FIG. 15B

SYSTEMS AND METHODS FOR ATRAUMATIC IMPLANTATION OF BIO-ACTIVE AGENTS

CROSS-REFERENCE TO RELATED APPLICATIONS

This application is a divisional under 35 U.S.C. §121 of U.S. patent application Ser. No. 10/894,810, filed Jul. 19, 2004 now U.S. Pat. No. 7,632,262 and entitled "Systems and Methods for Atraumatic Implantation of Bio-Active Agents," the entire contents of which are incorporated by reference herein.

FIELD OF THE INVENTION

The present invention relates to delivery systems and methods for delivering fragile bio-active agents, such as stem cells or myoblasts, into a target tissue using a passive or controlled injection deployment techniques that reduces trauma to the bio-active agent and/or collateral damage to the host tissue.

BACKGROUND OF THE INVENTION

Cardiovascular disease is the leading cause of death in the industrial world today. During the disease process, atherosclerotic plaques develop at various locations within the arterial system and restrict the flow of blood through the affected vessels. When such plaque develops within the blood vessels that feed the muscles and other tissues of the heart, myocardial infarctions and ischemia due to reduced blood flow to the heart tissues may result.

Over the past decades numerous devices and methods have been evaluated for preventing myocardial ischemia or cell death, including but not limited to: traditional surgical methods (e.g. open heart surgery), minimally invasive surgery, interventional cardiology (e.g. angioplasty, atherectomy, stents), and catheter based delivery of bioactive agents, including growth factors, genes and stem cells.

Open surgical methods for treating cardiovascular disease typically involve surgically accessing the heart to bypass blockages in the coronary blood vessels. Based upon the degree of coronary artery disease, a single, double, triple, or even greater number of vessels are bypassed by creating a conduit from the aorta or pedicle internal mammary artery to a stenosed coronary artery, at a location distal to the occluded site, using either synthetic or natural bypass grafts. Such procedures generally involve significant pain, extended rehabilitation time and high morbidity, and are time-consuming and costly to perform.

Minimally invasive surgical approaches have been developed wherein limited access is obtained to the heart and affected vessels using small incisions made through the ribs. While these methods reduce pain and rehabilitation time, they are available for a relatively limited number of procedures.

Interventional cardiology apparatus and methods, such as percutaneous transluminal coronary angioplasty (PTCA), rotational atherectomy, and stenting, have been developed to overcome some of the drawbacks of open and minimally-invasive surgical methods. While many patients are successfully relieved of symptoms with interventional procedures, a significant number of patients still experience irreversible myocardial injury related to abrupt closure or restenosis of the blood vessels within a relatively short period of time after the interventional procedure.

Work is currently in progress to develop advanced apparatus and methods, such as drug-coated stents, to delay or prevent restenosis. In addition, as described in *Local Drug Delivery for the Treatment of Thrombus and Restenosis*, IAGS Proceedings, J. Invasive Card., 8:399-408, October 1996, some practitioners augment standard catheter-based treatment techniques with devices that provide local delivery of medications to the treated site, with the goal of counteracting clotting, reducing inflammatory response, and blocking proliferative responses.

All of the foregoing methods are primarily intended to restore patency of a stenosed vessel thus improve blood flow to tissues downstream but cannot cause the muscle in the infarcted zones to regenerate. Transmyocardial revascularization was conceived as a method of supplementing the blood supply delivered to the heart by creating channels, either mechanically or by laser ablation, that extend from the endocardial surface of the left ventricle into the myocardial muscle. It was believed that such techniques could engender an angiogenic response, in which new blood vessels would form in the vicinity of the ventricular channels. The reported results for such techniques were disappointing, and such approaches have essentially been abandoned.

More recent efforts for regenerating healthy tissue in affected areas of the heart muscle involve percutaneous or direct injection of bioactive agents to the affected tissue areas, including gene vectors, growth factors, myoblasts and stem cells. For example, Mack et al., in an article entitled *Biologic Bypass with the Use of Adenovirus-Medicated Gene Transfer of the Complementary Deoxyribonucleic Acid for Vascular Endothelial Growth Factor 121 Improves Myocardial Perfusion and Function in the Ischemic Porcine Heart*, J. Thor. & Card. Surge 115:168-177 (January 1998) describes experiments to improve myocardial perfusion using growth factors. Sanborn et al., *Percutaneous Endocardial Gene Therapy: In Vivo Gene Transfer and Expression*, J. Am. Coll. Card. 33:262A (February 1999) describe the injection of angiogenic proteins and genes directly into the heart via the endocardium using a percutaneous fluoroscopically guided system. Uchida et al., *Angiogenic Therapy of Acute Myocardial Infarction by Intrapericardial Injection of Basic Fibroblast Growth Factor and Heparin Sulfate: An Experimental Study*, Am. Heart J. 130:1182-1188 (December 1995), describe growth factor injections into the pericardial cavity using a catheter system inserted through the right atrium. U.S. Pat. No. 5,244,460 to Unger et al. describes a method for infusing bioactive agents containing blood vessel growth promoting peptides (i.e. fibroblast growth factor) via a catheter inserted into a coronary artery.

Thompson et al., in *Percutaneous Transvenous Cellular Cardiomyoplasty*, J. Am. Coll. Card., 41(11):1964-1971 (June 2003), describe apparatus and methods for pressurized injection of cultured autologous bone marrow cells, suspended in a biodegradable biogel polymer, into the myocardium using percutaneous access via the coronary sinus. An ultrasound-guided catheter was used to place a needle into a coronary vein, the needle was then extended into the myocardium, and a floppy catheter disposed within the needle was advanced into the myocardium to deliver the bone marrow cells. The article describes that the biodegradable polymer is used to reduce physical compression and lysis of the cells as they are injected into the target tissue.

U.S. Patent Application Publication No. US 2003/0191449 to Nash et al. describes a system for pressurized endocardial injection of bioactive materials, including growth factors, stem cells, etc., into the myocardial tissue using an endocardial approach. U.S. Pat. No. 6,432,119 to Saadat describes methods and apparatus for endocardial delivery of autologous angiogenic substances to myocardium in connection with mechanical percutaneous transmyocardial revascularization. U.S. Pat. No. 6,120,520 to Saadat et al. describes a system for providing endocardial injection of bioactive agents from a pressurized source.

As noted in the foregoing Thompson article, needle withdrawal in the preceding systems may provide an exit point for cells or gene therapy substrates to be released into systemic circulation, with a concomitant risk of embolization. In addition, pressurized injection of certain bioactive agents, such as stem cells, is expected to inflict physical damage to the cell membranes due to fluid turbulence and pressure fluctuations encountered during the injection process (referred to herein as "barotrauma"), resulting in lysis of the cells that may significantly reduce the yield of viable cells delivered at the injection site and/or trauma to the target tissue.

Further, depending upon the degree of pressure-regulation of the injection system, it may in addition be possible for some of the injected bioactive agent to be expelled from the needle track during the injection process, e.g., due to systolic muscle contraction. Forceful injection of any material into tissue also may disrupt the delicate intercellular matrix, thereby causing target tissue cellular injury. Also, if a needle were to be inadvertently inserted into a small myocardial vessel, forceful injection may result in shear stress injury to the vessel or embolization to the pulmonary artery or remote tissue.

In view of these drawbacks of previously known devices, it would be desirable to provide methods and apparatus for delivering bioactive agents, especially fragile bioactive agents, in such a way that reduces the risk of inflicting barotrauma on the bioactive agent and target tissue during delivery while at the same time minimizing the risk of embolization It further would be desirable to provide methods and apparatus for delivering bioactive agents, especially fragile bioactive agents, that reduces the need for biodegradable carriers, such as biogels, to cushion delivery of the bioactive agents, thus reducing the risk of embolization resulting from release of such material into systemic circulation while also preserving the integrity of the target tissue.

It further would be desirable to provide methods and apparatus for delivering cells to damaged tissue to promote tissue regeneration, wherein the delivery systems and methods reduce physical trauma to the cell membranes during delivery, and enhance the proportion of viable cells delivered to the damaged tissue.

SUMMARY OF THE INVENTION

In view of the foregoing, it is an object of the present invention to provide methods and apparatus for delivering bioactive agents that reduces the risk of inflicting barotrauma on the bioactive agent or target tissue during delivery.

It is another object of this invention to provide methods and apparatus for delivering bioactive agents, especially fragile bioactive agents, that reduces the need for biodegradable carriers, such as biogels, to cushion delivery of the bioactive agents, thus reducing the risk of embolization resulting from release of such material into systemic circulation.

It is a further object of the present invention to provide methods and apparatus for delivering cells to damaged tissue to promote tissue regeneration, wherein the delivery systems and methods reduce physical trauma to the cell membranes during delivery, and enhance the proportion of viable cells delivered to the damaged tissue.

These and other objects of the present invention are accomplished by providing methods and apparatus for delivering bioactive agents, especially fragile bioactive agents, wherein the bioactive agent is atraumatically deployed in a needle track formed in a target tissue mass following formation of the needle track. In the context of the present invention, "atraumatic" deployment means deployment of the bioactive agent without generating turbulent fluid motion that inflicts physical damage to the bioactive agent, e.g., due to high shearing stresses or pressure fluctuations.

In accordance with the principles of the present invention, deployment of bioactive agents is accomplished using needle arrangements that avoid impingement of the bioactive agent against target tissue at high velocity or employ capillary action to draw the bioactive agent out of the needle during needle withdrawal. Alternatively, the present invention could hold the column of biologic material stationary utilizing a proximal syringe or internal piston while the needle is being retracted. While the present invention is described in the context of promoting regeneration of myocardial tissue, the apparatus and methods of the present invention may be advantageously employed wherever it is desired to promote tissue regeneration.

In accordance with a first aspect of the present invention, apparatus is provided for delivering a bioactive agent, such as a suspension of stem cells, into the myocardium through the endocardial surface. The apparatus preferably comprises a catheter that may be deployed in the left ventricle, and a needle disposed from the catheter and configured to be selectively extended into the myocardium through the endocardial surface to a predetermined maximum depth.

In a first embodiment, the apparatus further comprises a delivery system that applies and dispenses the bioactive agent while simultaneously retracting the needle from a maximum predetermined depth, so that the stem cell suspension is deployed along the needle track. In a preferred embodiment, the delivery system provides no positive pressure to inject the bioactive agent, but merely enables the bioactive agent to be drawn out of the distal tip of the needle, during needle retraction, by capillary action. Alternatively, the needle may be advanced having a column of fluid disposed within it, and the column of fluid may then be held stationary while the needle is retracted.

In an alternative embodiment, the needle further comprises means for creating a tissue space surrounding a distal or lateral surface of the needle, thereby permitting bioactive agent to be infused into the space without retracting the needle. The means for creating the tissue space may take the form of one or more expandable struts that are deployed to create a space surrounding the needle, and permit the bioactive agent to be infused into apertures that rest in a lateral surface of the needle. Alternatively, the needle may be fluted or grooved, so that the outer edges of the flutes support the tissue and form a space into which the bioactive agent may be infused via apertures at the base of the flutes.

The catheter system of the present invention further may include a structure for positioning and stabilizing the needle against the endocardial surface during infusion of the bioactive agents. This structure may comprise one or more guide rails that transition from a contracted delivery configuration to a deployed configuration in the ventricular chamber, such as have been developed for transmyocardial revascularization. Alternatively, the positioning and stabilizing structure may comprise a relatively flexible catheter and a plurality of pre-formed stylets that are configured to be selectively inserted into the flexible catheter to conform the catheter to specific regions of the cardiac chambers.

In accordance with another aspect of the present invention, apparatus is provided for delivering a bioactive agent, such as a suspension of stem cells, into the myocardium through the epicardial surface via access from the cardiac veins. In this embodiment the apparatus preferably comprises a catheter that may be deployed via deep vein through the inferior or superior vena cava into the coronary sinus, great cardiac vein and adjoining vessels. A needle disposed from a distal or lateral surface of the catheter is configured to be selectively extended into the myocardium through the epicardial surface to a predetermined depth. Infusion of bioactive agents into the myocardium may be accomplished either by depositing the agent into the needle track while withdrawing the needle (or holding the column of fluid stationary while retracting the needle) or by creating a tissue space surrounding the needle as described for the endocardial access embodiment.

The needle exit port of the catheter may be directed towards the myocardium using a positioning balloon disposed on the opposite side of the catheter from the exit port, so that when the balloon is inflated it preferentially turns the device inward. Similarly the exit port could be directed inward using fluoroscopy, electrical mapping or intravascular ultrasound.

Methods of using the catheters of the present invention, for example, to promote regeneration of cardiac and other tissues also are provided.

BRIEF DESCRIPTION OF THE DRAWINGS

Further features of the invention, its nature and various advantages will be more apparent from the accompanying drawings and the following detailed description of the preferred embodiments, in which:

FIG. 13 depicts the arrangement of the coronary veins in a human heart;

FIG. 14 shows a distal end of a catheter of the present invention suitable for use in delivering bioactive agents to the myocardium via the coronary veins; and FIGS. 15A and 15B illustrate a method of using the apparatus of FIG. 14 to deliver bioactive agents to the myocardium via the coronary veins.

DETAILED DESCRIPTION OF THE INVENTION

The present invention is directed to methods and apparatus for delivering bioactive agents, especially fragile bioactive agents, by atraumatically depositing the bioactive agent in a needle track formed in a target tissue mass, following formation of the needle track. In the context of the present invention, "atraumatic" deployment refers to deploying the bioactive agent without the generating turbulent fluid motion that inflicts physical damage to the bioactive agent or target tissue, e.g., due to high shearing stresses or pressure fluctuations ("barotrauma").

In accordance with the principles of the present invention, deployment is accomplished using needle arrangements that avoid impingement of the bioactive agent against target tissue at high velocity, or capillary action, which draws the bioactive agent out of the needle during needle withdrawal. Alternatively, a column of bioactive agent disposed within the needle may be advanced in unison with the needle, and then held stationary or a low volume is injected forward while the needle is retracted, thereby during insertion of the needle, controlled by a proximal deploying the bioactive agent without pressurized injection. Alternatively, or in addition, the needle may comprise expandable struts or grooves for creating a tissue space surrounding a distal or lateral surface of the needle, thereby permitting bioactive agent to be infused into the space without retracting the needle.

Figure 1A:
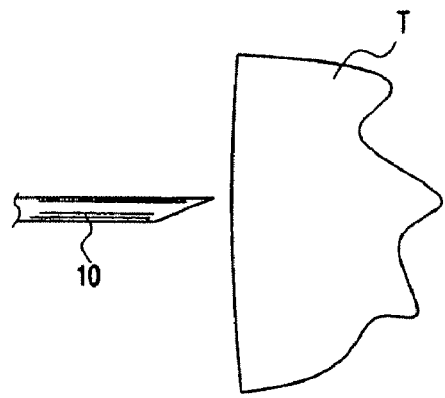
FIGS. 1A-1C are views depicting previously known methods of injecting drugs and other bioactive agents into a tissue mass.
Figure 1B:
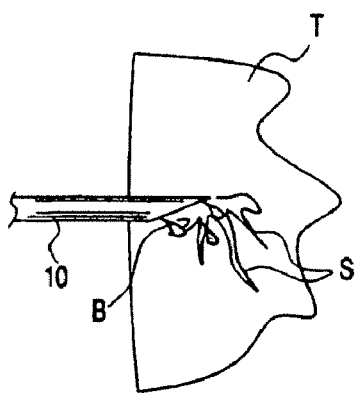
Figure 1C:
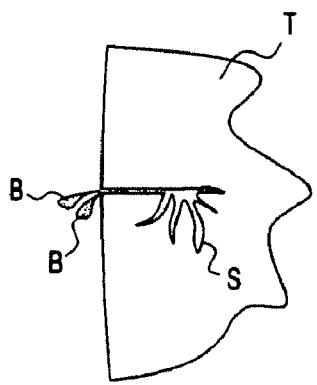

Referring to FIGS. 1A-1C, some of the drawbacks of previously known bioactive agent delivery systems are described. As discussed above, some researches currently are investigating regeneration of tissue, e.g., heart tissue, by injecting stem cells into the tissue to promote angiogenesis or the formation of new heart tissue. FIG. 1A illustrates previously known injection needle 10 being brought into approximation with tissue mass T, such as the endocardial surface of the left ventricle.

Once the tip of needle 10 is inserted into the tissue, as shown in FIG. 1B, bioactive agent B, such as a drug, is injected into the tissue mass. Applicant has concluded that pressurized injection of the bioactive agent may have a substantial detrimental effect both on the agent delivered and the tissue to be treated. With respect to the tissue, applicant has observed that pressurized injection of fluid may cause the tissue to tear along naturally-occurring striations S, thus weakening the muscle. In addition, the bioactive agent is expected to pool along the membrane surfaces of the striations.

Applicant also has observed that pressurized injection also causes turbulence that causes the injectate stream to impinge violently against the tissue as it leaves the tip of the injection needle. In addition, the injectate may experience rapid pressure fluctuations. These effects may lyse the bioactive agent, particularly where the agent comprises stem cells, by rupturing the cell membrane or damaging the cellular components. Applicant therefore has theorized that a much higher yield of viable cells may be delivered to a target tissue if apparatus and methods could be provided to avoid stationary pressurized injection.

One approach suggested by researchers in the field of stem cell injection is to suspend the stem cells in a biocompatible gel to cushion the cells during injection. As discussed above with respect to the Thompson article, this approach presents the potential for the injectate to exit the needle track and embolize. As illustrated in FIG. 1C, once needle 10 has been withdrawn from the needle track N, systolic muscle contraction may cause some of the injected bioactive agent B to be expelled from the needle track. If a biogel were used, this could result in thrombus formation with potentially dire consequences for the patient.

Figure 2A:
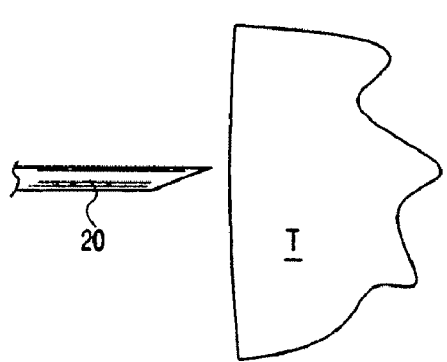
FIGS. 2A-2C are views depicting a method of injecting drugs and other bioactive agents into a tissue mass in accordance with the principles of the present invention.
Figure 2B:
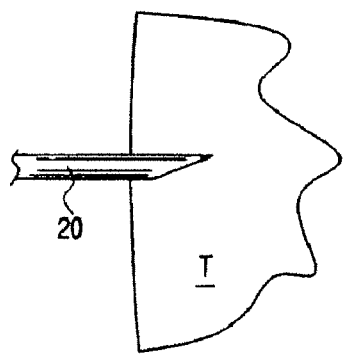
Figure 2C:
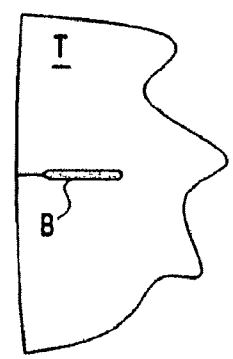

Referring now to FIGS. 2A to 2C, apparatus and methods of the present invention are described that overcome the drawbacks of previously known systems for delivering fragile bioactive agents, such as stem cells. As shown in FIG. 2A, in accordance with the principles of the present invention, needle 20 is first approximated to endocardial tissue mass T. In FIG. 2B, needle 20 is shown inserted into the tissue mass. In FIG. 2C, as needle 20 is withdrawn from the tissue mass, bioactive agent B is drawn out of the tip of the needle and deposited in the needle track.

Because in the present invention the bioactive agent is not injected under pressure into the tissue, there will be substantially less turbulence and pressure fluctuation imposed on the agent as it exits needle 20. Also, the bioactive agent will not damage the tissue mass by splitting the tissue along the naturally-occurring striations, as in FIG. 1B. In addition, because a pool of bioactive agent will not accumulate along the striations, there is less risk that the bioactive agent will be expelled from the tissue during cardiac contractions. Also, retraction of the needle will minimize the risk of inadvertent injection of the full load into a vessel.

Figure 3A:
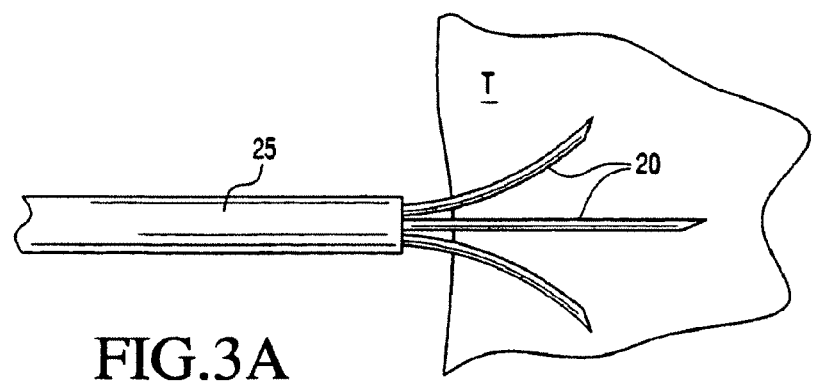
FIGS. 3A and 3B are views depicting an alternative method of the present invention for injecting drugs and other bioactive agents into a tissue mass.
Figure 3B:
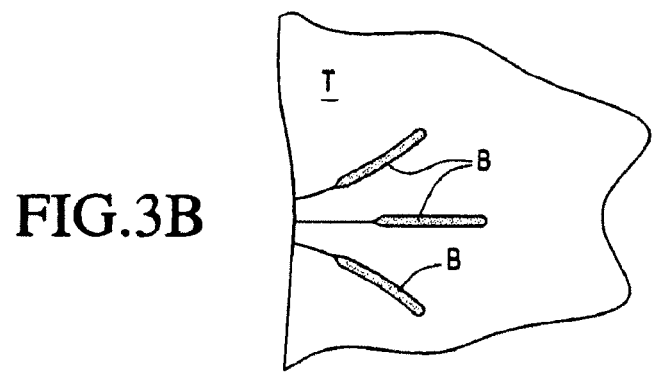

FIGS. 3A and 3B illustrate catheter 25 having multiple needles 20 that curve away from one another when inserted in tissue mass T. Catheter 25 is arranged so that the needles may be simultaneously extended into the tissue mass to form needle tracks, as depicted in FIG. 3A. Needles 20 then are retracted, so that bioactive agent B is drawn from the needle tips by capillary action. As depicted in FIG. 3B, an arrangement of multiple needles will permit a larger area of the tissue mass to receive the stem cells for a single actuation of catheter 25.

Although three needles 20 are illustrated in FIG. 3, it will be understood that any number of needles may be used in the accordance with the principles of the present invention. For example, according to some embodiments, a spiral needle is rotated into the muscle mass and rotated in the opposite direction as the biologic agent is released. More particularly, as the spiral shaped needle is advanced, it will rotate in a first direction and "corkscrew" into the muscle. As the needle is rotated in the opposite direction, the biologic agent is injected as the needle retracts. Such an injection during retraction mechanism advantageously can be used to inject the liver or other organ from an endovascular (catheter) approach or a non-catheter transmutations approach.

Figure 4A:
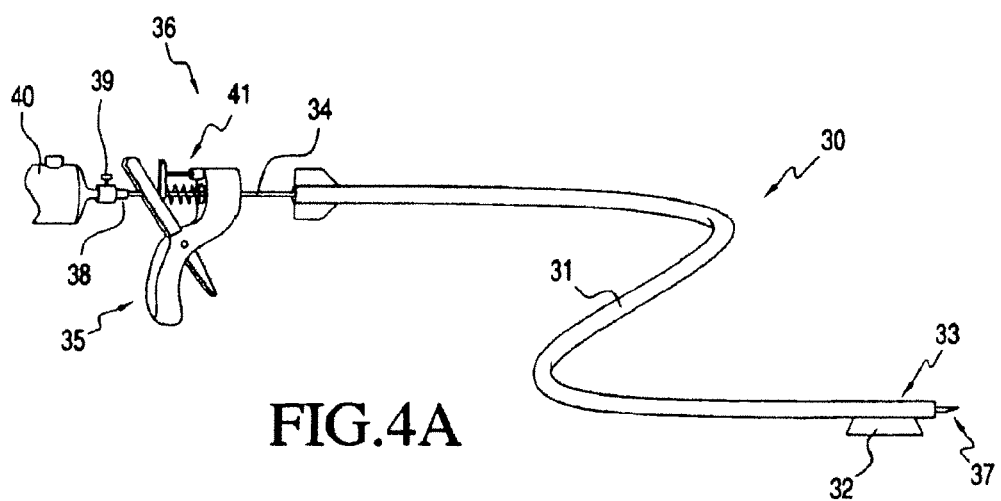
FIGS. 4A and 4B depict, respectively, a side view of apparatus of the present invention and a detailed view of the handle portion.

Referring now to FIG. 4A, delivery system 30 of the present invention is described. Delivery system 30 comprises catheter 31, elongated needle 34 and handle 35. Catheter 31 preferably includes guide member 32 disposed adjacent to distal tip 33, which permits the distal end of the catheter to be slidably coupled to a guide rail, as described hereinbelow with respect to FIGS. 8-11.

Elongated needle 34 is slidably disposed within a lumen of catheter 31, and includes handle 35 disposed in proximal region 36 and tissue-piercing tip 37 that may be selectively extended beyond the distal end of catheter 31. Needle 34 includes an internal lumen that extends from the proximal end 38 of the needle to tip 37. Proximal end 38 is coupled via valve 39 to vial 40 containing a suitable bioactive agent, such as a suspension of stem cells. Handle 35 includes mechanism 41 that reciprocates distal tip 37 of the needle to form a needle track, and facilitates delivery of bioactive agent from vial 40 through a lumen of needle 34 to the targeted tissue.

Figure 4B:
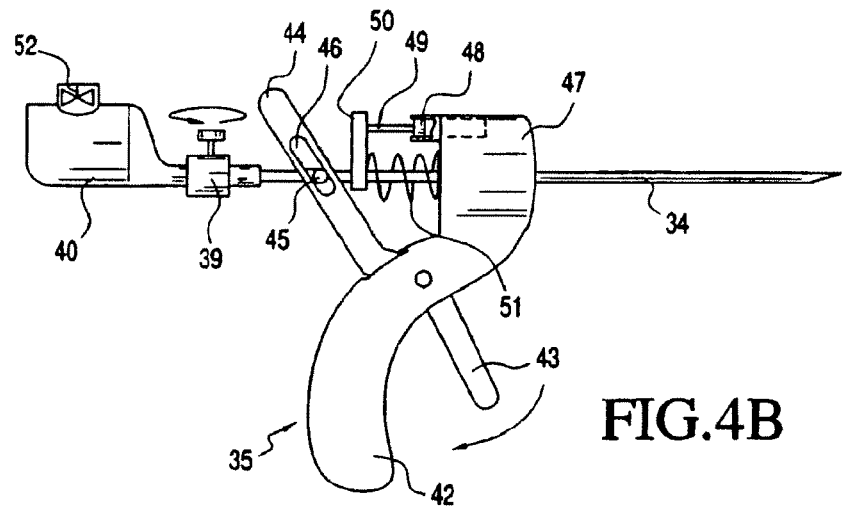

As shown in FIG. 4B, handle 35 comprises grip 42 carrying pivotally mounted lever 43. Needle 34 is coupled to upper portion 44 of lever 43 via pin 45 that is disposed to slide in slot 46 of upper portion 44. Grip 42 includes upper portion 47 that carries piston 48. Rod 49 of piston 48 is coupled to block 50 that is fixedly mounted to needle 34. Spring 51 is disposed over needle 34 and is captured between block 50 and upper portion 47 of grip 42, and biases rod 49 to its extended position.

Valve 39 selectively couples vial 40 to the lumen of needle 43, and is operated by the clinician during actuation of handle 35 to deploy bioactive agent in the needle track formed by the distal tip of the needle. According to some embodiments, the device is modified such that valve 39 automatically releases during needle withdrawal. Vial 40 preferably includes one-way valve 52 that permits bioactive agent to be drawn from the vial during retraction of the needle from the tissue mass.

In operation, handle 35 is held by the clinician so that, after distal region 33 of catheter 31 is disposed proximate a tissue mass, lever 43 may be depressed. This causes the distal tip of the needle to be extended into the tissue mass while simultaneously compressing spring 51 and compressing piston 48. The clinician then opens valve 39 to couple the bioactive agent, e.g., suspension of stem cells, to the lumen of needle 34, and releases lever 43. Alternatively, valve 39 may be a one-way valve that permits bioactive agent to flow from vial 40 into the needle, but prevents reverse flow. In this case, valve 39 would open automatically during needle retraction, but would remain closed during needle insertion.

When the clinician releases lever 43, spring 51 urges block 50 in the proximal direction, thereby retracting distal tip 37 of the needle from the needle track. The rate at which the spring returns the upper portion 44 of lever 43 to its proximal-most position is determined by piston 48. This return rate preferably is selected to cause a desired amount of bioactive agent to be deposited in the needle track, without damaging the tissue or creating the potential for leakage of the bioactive agent into the left ventricle via the needle track entrance.

Valve 39 and one-way valve 52 are used to control the deposition of the bioactive agent from needle 34 during formation of the needle track and retraction of the needle. In particular, valve 39 is closed during extension of needle 34, so that the column of bioactive agent in the lumen of the needle is substantially incompressible, and prevents a tissue core from entering and occluding the distal tip of the needle. Once lever 43 has been compressed to cause a desired extension the needle tip into the tissue mass, valve 39 couples the needle lumen to the contents of vial 40. One-way valve 52 ensures that during retraction of the needle, a negative pressure does not develop within vial 40 that could impede having the bioactive agent drawn from the distal tip of the needle by capillary action.

Before the distal tip of needle 34 retracts from within the needle track, valve 39 closes to decouple vial 40 from the lumen of needle 34. This prevents the bioactive agent from being deposited at the needle track entrance, and reduces the risk that the bioactive agent will be ejected from the needle track entrance and embolize. Catheter 31 may then be repositioned, and the above process repeated. Depending upon the selection of valve 39, operation of valve 39 may be controlled by the physician or may be arranged to operate automatically.

Figure 5:
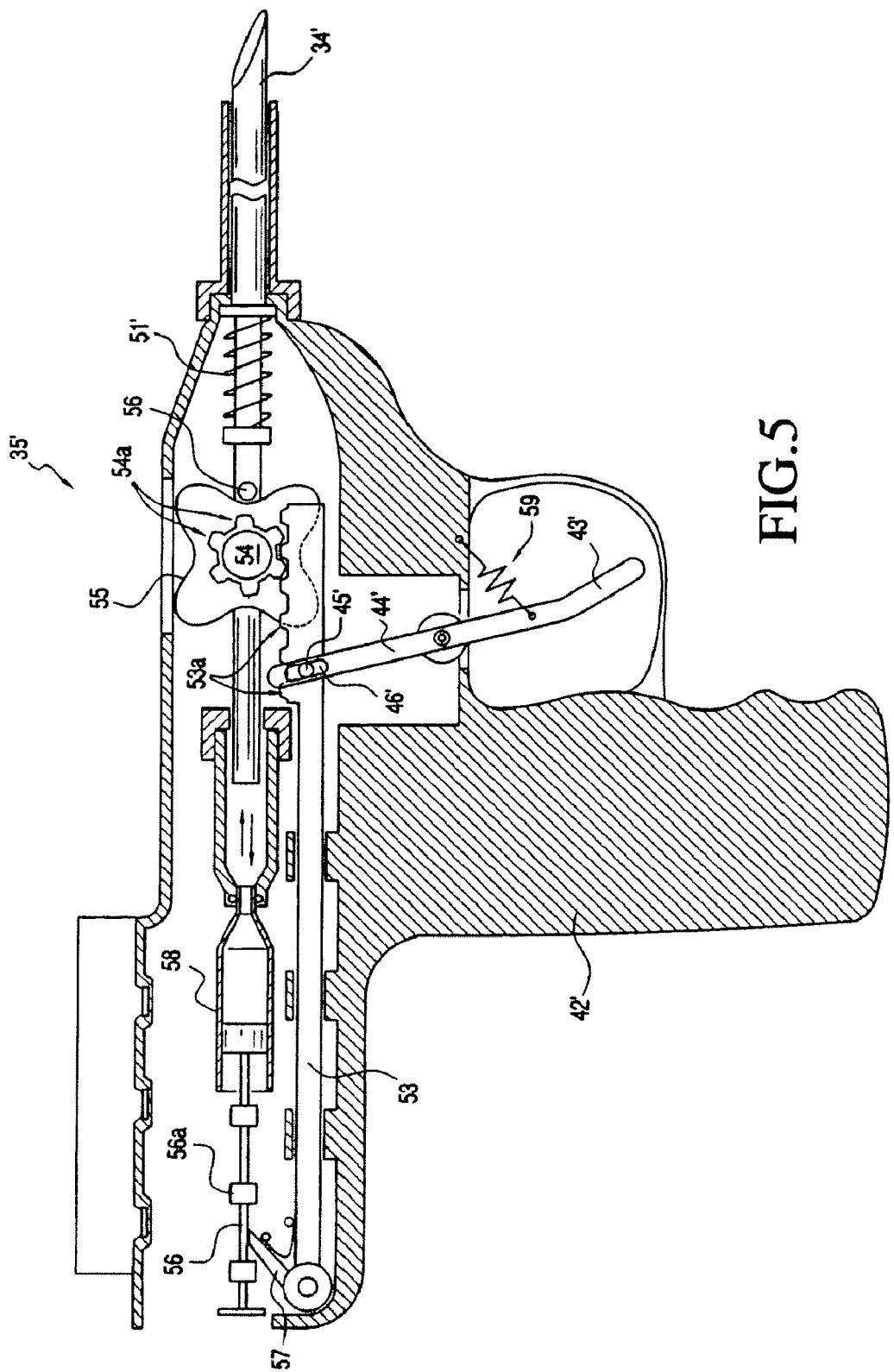
FIG. 5 depicts a detailed view of an alternative handle portion suitable for use with the apparatus of the present invention.

Referring to FIG. 5, an alternative handle portion suitable for use with the apparatus of the present invention will now be described. Handle 35' comprises grip 42' carrying pivotally mounted lever 43'. An upper portion 44' of grip 42' is attached to a ratchet member 53 via pin 45', which is disposed to slide within slot 46' of upper portion 44'. Ratchet member 53 includes a distal end having a plurality of notches 53a that are dimensioned to receive corresponding teeth 54a projecting from gear 54. Gear 54 is selectively coupled to lobed cam 55 so that rotation of gear 54 in a counterclockwise direction causes cam 55 to rotate in a counterclockwise direction. However, when gear 54 is rotated in a clockwise direction, it does not engage cam 55, but instead spins freely.

Needle 34' preferably includes pin 56 attached thereto such that a quarter turn of cam 55 initially forces the needle distally, and then permits the needle to retract proximally to its original position under the force of spring 51'. As the needle retracts, plunger 56 is urged distally by spring-loaded arm 57, which is pivotally attached to a proximal end of ratchet member 53. More particularly, the distal movement of ratchet member 53 forces spring-loaded arm 57 into contact with projection 56a on plunger 56, thereby forcing bioactive agent disposed within syringe 58 to be forced through the needle lumen and ejected from the distal tip only during retraction of the needle from the tissue mass. After the clinician releases the lever, spring 59 returns the lever to its original position and ratchet member 53 is urged proximally back to its original position. Since gear 54 does not engage cam 55 during clockwise rotation, needle 34' does not move as lever 43' is returned.

In operation, the distal region of the delivery catheter is disposed proximate a target tissue. Handle 35' is held by the clinician and lever 43' is depressed, thereby causing the ratchet member to move proximally. Proximal movement of ratchet member 53 rotates the gear and cam 55, thus causing the distal tip of the needle to be extended into the tissue mass. However, the bioactive agent is not injected into the tissue mass at this time due to a predetermined amount of spacing between spring-loaded arm 57 and plunger projection 56a. As the clinician further depresses the lever, the needle is retracted (due to the lobed shape of cam 55), and continued distal movement of the ratchet member causes spring-loaded arm 57 to contact projection 56a and depress the plunger. Thus, the bioactive agent is injected during needle retraction rather than during needle insertion.

Figure 6A:
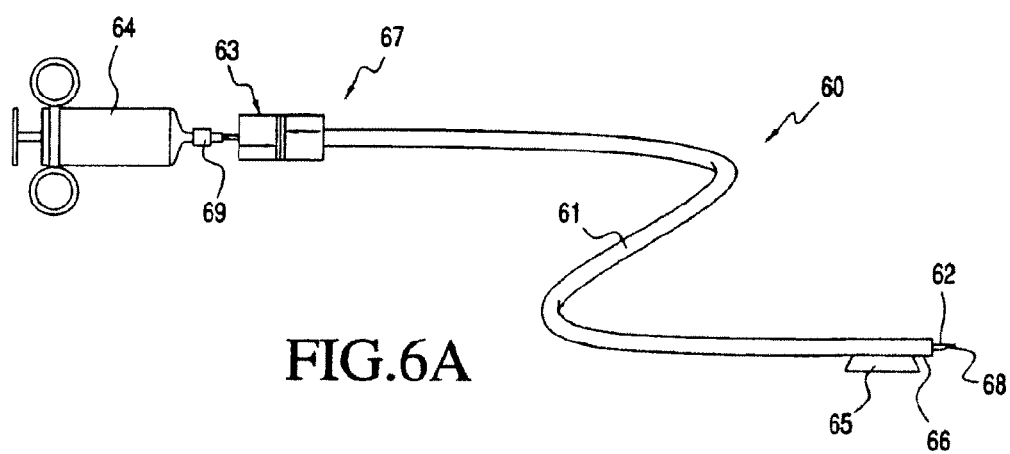
FIGS. 6A and 6B depict, respectively, a side view of alternative apparatus of the present invention and a detailed view of the handle portion that device.
Figure 6B:
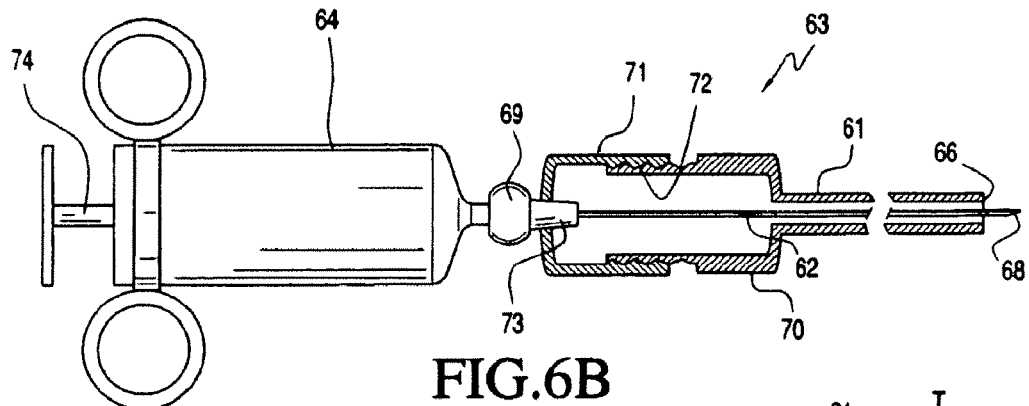

Referring to FIGS. 6A and 6B, an alternative embodiment of a delivery system constructed in accordance with the principles of the present invention is described. Delivery system 60 comprises catheter 61, elongated needle 62, handle 63 and syringe 64. As for the previous embodiment, catheter 61 preferably comprises guide member 65 disposed adjacent to distal tip 66, so that catheter 61 may be slidably coupled to a guide rail, as described hereinbelow with respect to FIGS. 8-11.

Elongate needle 62 is slidably disposed within a lumen of catheter 61, and is coupled to handle 63 disposed in proximal region 67 and tissue-piercing tip 68 that may be selectively extended beyond the distal tip 66 catheter 61. Needle 62 includes an internal lumen that extends from its proximal end to tip 68. The proximal end of needle 62 is coupled via fitting 69 to syringe 64. Syringe 64 contains a suitable bioactive agent, such as a suspension of stem cells. Handle 63 is configured to selectively extend and retract tip 68 of the needle to form a needle track.

With respect to FIG. 6B, handle 63 comprises body portion 70 coupled to actuator 71 via threaded portion 72. Needle 62 is affixed only to actuator 71 at base 73, and freely translates through body portion 70 when the actuator 71 is rotated on threaded portion 72. In this manner, needle 62 may be reciprocated through a predetermined distance by rotating actuator 71 relative to body portion 70, thereby extending and retracting tip 68 of needle 62 through that predetermined distance.

Syringe 64, may be conventional in construction and preferably includes piston 74 disposed within the syringe so that forward movement of the piston ejects the contents of the syringe into the lumen of needle 62. Once tip 68 of needle 62 has been extended into a tissue mass, piston 74 of syringe 64 is actuated to dispense bioactive agent from the syringe into the needle track.

Figure 7A:
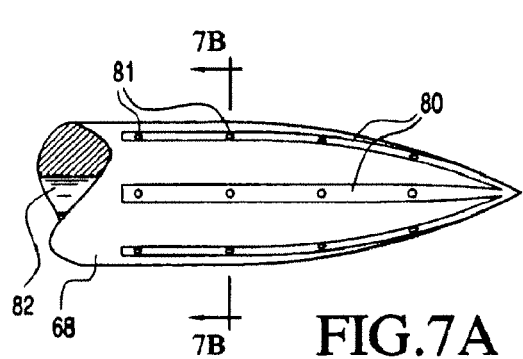
FIG. 7A is a side view of an alternative distal tip of a needle suitable for use in the apparatus of FIGS. 4 and 5.
Figure 7B:
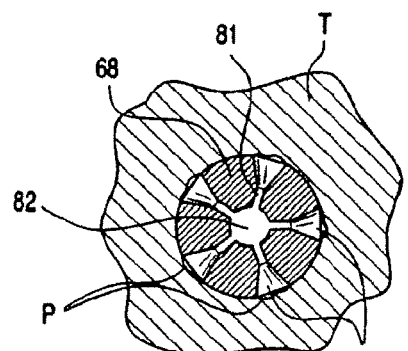
FIG. 7B is a cross-sectional view of FIG. 7A.

Referring now also to FIGS. 7A and 7B, in accordance with the principles of the present invention, tip 68 is configured to reduce barotrauma and the imposition of high shears stresses on the bioactive agent during delivery into the needle track. Tip 68 of needle 62 illustratively includes V-shaped grooves 80 that extend inwardly from the surface of the needle. As shown in FIG. 7B, apertures 81 are disposed in grooves 80 and communicate with lumen 82, which extends back to handle 63 where the lumen communicates with syringe 64 (see FIG. 6B). When extended into tissue T, grooves 81 suspend the tissue away from the exterior surfaces of the grooves, to create pockets P into which the bioactive agent may be deposited. In this manner, the bioactive agent may be deposited in pockets P formed within tissue T using a low pressure injection, and are not subjected to high shear stresses as the bioactive agent impinges upon the surrounding tissue.

Operation of the apparatus of FIGS. 6 and 7 is as follows. Once the clinician has located tip 66 of catheter 61 proximate to a desired tissue mass (for example, as with respect to FIGS. 9-12 below), body portion 70 of handle 63 is held stationary while actuator portion 71 is rotated on threaded portion 72. Rotation of actuator 71 causes needle 62 to advance through body portion 70 to extend tip 68 of the needle into the tissue mass, as illustrated in FIG. 2B. As illustrated in FIG. 7B, this causes the tissue to become tented over grooves 81. The clinician then slowly depresses piston 74 of syringe 64 to cause the bioactive agent to flow through lumen 82 of the needle and exit through apertures 81 to fill grooves 81.

After piston 74 has been depressed a desired distance, actuator 71 is rotated in the reverse direction to withdraw tip 68 from the needle track, thereby leaving the bioactive agent deposited within the needle track. Piston 74 of syringe 64 either may be gently depressed during rotation of actuator 71, so that additional bioactive agent is drawn through grooves 81 and lumen 82 by capillary action, or alternatively the piston of the syringe may be moved to a position where no additional bioactive agent is dispensed within the needle track during withdrawal of the tip 68. Catheter 61 then may be repositioned within the organ and the process repeated.

Figure 8A:
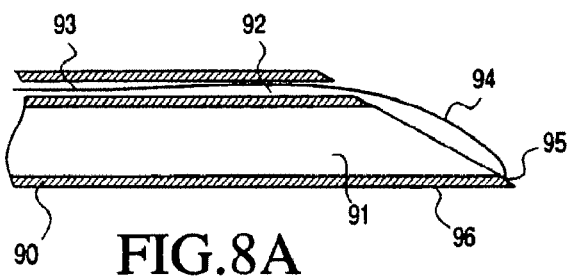
FIGS. 8A and 8B are side views of an alternative distal tip of a needle suitable for use in the apparatus of FIGS. 4-6.
Figure 8B:
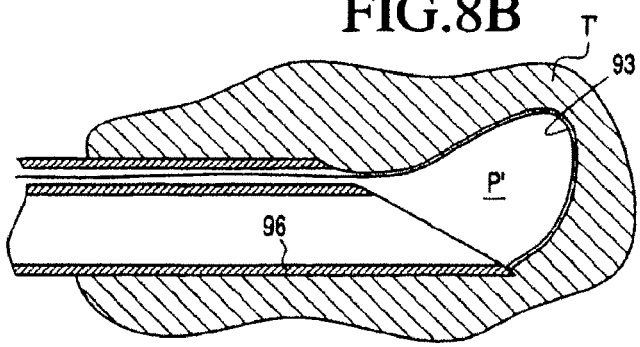

Referring now to FIGS. 8A and 8B, an alternative embodiment of a needle suitable for use in the delivery system of the present invention is described. The proximal portion of needle 90 is similar in construction to needle 62 of FIG. 6, and is coupled at its proximal end to a handle, such as shown in FIG. 6, that enables needle 90 to be extended into a tissue mass. Needle 90 comprises 91 through which bioactive agent may be dispensed from a syringe coupled to the handle, and further comprises lumen 92 that extends the full length of the needle.

Wire 93 is slidably disposed in lumen 92 with its proximal end coupled to an actuator button on the handle and distal end 94 extending across and affixed to portion 95 of tip 96 of the needle. Wire 93 is arranged so that it may be selectively translated distally through lumen 92 by actuating the button on the handle. When extended, wire 93 bows away from the tip 96, and creates pocket P' in tissue T', adjacent to tip 96. Wire 93 therefore functions in a manner similar to grooves 81 of the embodiment of FIG. 7, and enables the bioactive agent to be deposited into the needle track with little or no mechanical stress or barotrauma.

Operation of needle 90 is similar to that described hereinabove for the embodiment of FIG. 7, except that wire 93 is deployed prior to deposition of the bioactive agent. In addition, wire 93 preferably is collapsed to its contracted state before withdrawal of needle 90 from the needle track.

Figure 9A:
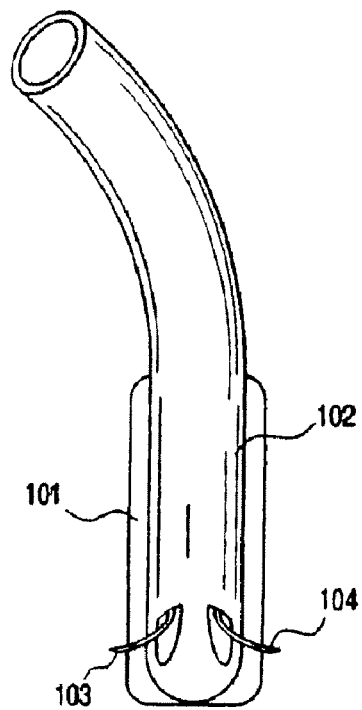
FIGS. 9A-9C are views of a guide system suitable for use with the catheters of FIGS. 4-6 for use in delivering bioactive agents to the interior of a hollow organ.
Figure 9B:
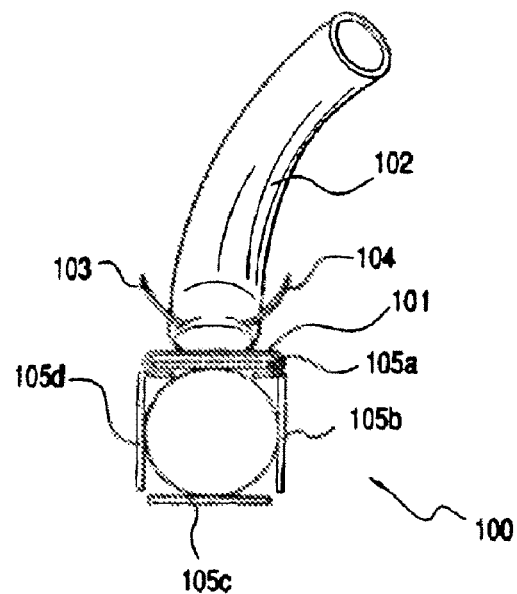
Figure 9C:
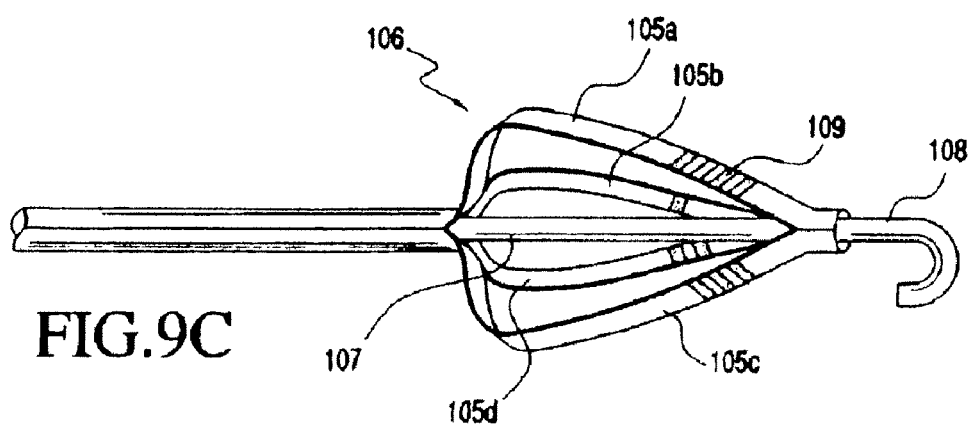

Turning to FIGS. 9A-9C, a more detailed description of guide members 32 and 65 of the delivery system of the present invention is presented. As discussed hereinabove with respect to catheter 31 of the delivery system of FIG. 4 and catheter 61 of the delivery system of FIG. 6, guide members 32 and 65, respectively, are provided for guiding positioning of the needle during insertion into a hollow body organ, such as the left ventricle of the heart. The use of guide systems has been proposed in the art for transmyocardial revascularization systems, and such guide systems may be advantageously employed in the context of the present invention.

FIGS. 9A and 9B are side and end views, respectively, of a guide member and guide system suitable for use with the delivery system of the present invention. Guide system 100 illustratively includes guide member 101 disposed on a distal region of catheter 102, wherein the catheter carries two selectively extendable and retractable needles 103 and 104 such as described hereinabove. Guide member 101 comprises a U-shaped channel that may be engaged to freely translate along preformed rail 105a.

As illustrated in FIG. 9C, four rails 105a, 105b, 105e and 105d may be joined at their distal ends to form cage 106 that may be expanded within a hollow-body organ to position the distal tip of catheter 102 at a selected position adjacent to the interior surface of the organ. Cage 106 may be advanced along guide wire 107 having atraumatic J-shaped tip 108. Each of rails 105a-105d may include one or more radio-opaque markers 109, that permit the rails to be distinguished one from the other under fluoroscopic imaging.

An illustrative use of the apparatus of the present invention to deliver a bioactive agent, such as stem cells, to an infarcted portion of a patient's heart is now described. First, guide wire 107 is advanced into the patient's left ventricle via a femoral artery and the descending aorta. Cage 106, which may be constrained in a contracted delivery configuration within a sheath, then is advanced along guide wire 107 until it is disposed within the left ventricle, for example, as confirmed by fluoroscopy. The sheath is then retracted to permit cage 106 to deploy to its expanded state, wherein rails 105a to 105d expand outwardly into contact with the endocardial surface.

Next, guide member 100 of catheter 102 is engaged with a selected one of rails 105a-105d, and advanced along the rail into the left ventricle. Once the position of the distal tip of the catheter is confirmed within the left ventricle, the needle may be extended to deposit the bioactive agent within the myocardium, as described above for the embodiments of FIGS. 4-6. Once the needle is retracted, the catheter may be repositioned along the same rail, or withdrawn and reinserted along one of the other rails, to repeat the process of depositing bioactive agent at selected sites with the myocardium. The cage can be recaptured in the retrieval sheath and rotated slightly before being released again allowing homogenous target myocardial treatment. Upon completion of this process, the catheter is removed, and the sheath may be reinserted to collapse and remove cage 106. Guide wire 107 then may be removed.

Figure 10A:
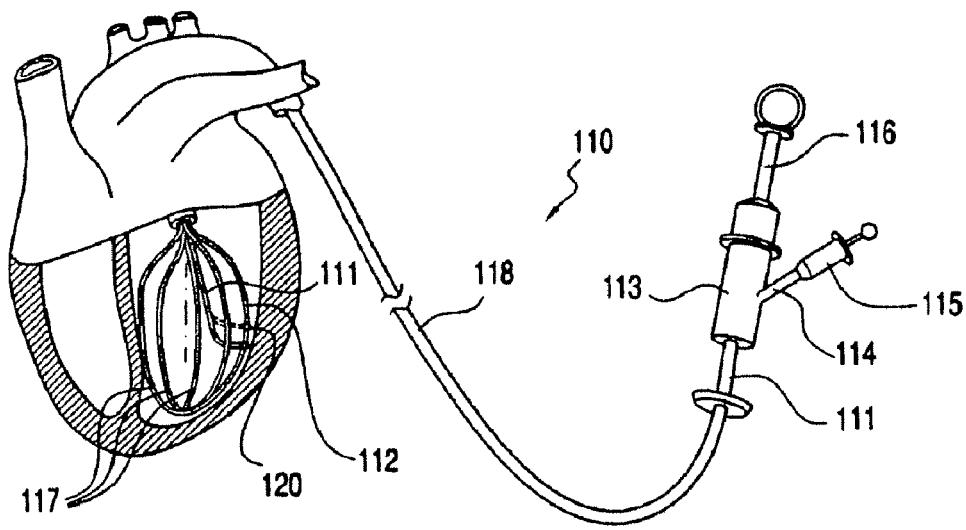
FIGS. 10A and 10B are, respectively, a side view of the catheter of the present invention engaged with an alternative guide system and a detailed view of the distal end of the guide system.
Figure 10B:
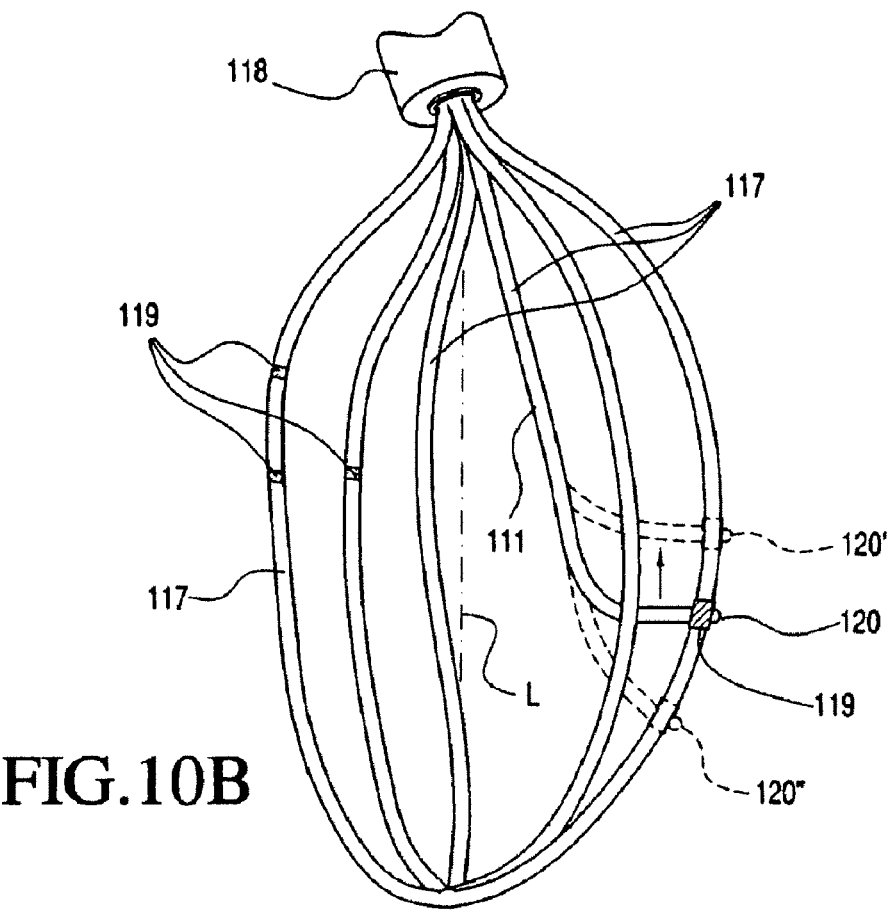

Referring now to FIGS. 10A and 10B, a delivery system of the present invention that uses an alternative guide system is described. Delivery system 110 includes catheter 111, similar in construction to that of FIG. 6, and configured to be advanced along guide system 112 similar to that described in U.S. Pat. No. 5,830,210 to Rudko et al. Catheter 111 includes handle 113 at its distal end and includes side port 114 to which syringe 115 containing a suitable bioactive agent may be coupled. Guide system includes proximal end 116 and plurality of rails 117 at its distal end. Sheath 118 is slidable disposed over rails 117 and may be selectively advanced or retracted to transition the rails between a deployed configuration, where the rails expand into contact with the endocardial surface, and a contracted configuration. Rails 117 may include different numbers of radio-opaque markers 119 to distinguish the rails form one another under fluoroscopic imaging.

Catheter 111 includes guide member 119 slidably coupled to a selected one of rails 117, so that the distal end of the catheter may be selectively positioned along the rail. Needle 120, of which only the distal tip is visible in FIG. 10B, may be selectively extended and retracted to deposit bioactive agent within the myocardium as described hereinabove with respect to the embodiment of FIG. 6. Accordingly, guide system 112 permits the delivery system to be positioned as shown in solid line by needle 120 to deliver bioactive agent into the myocardium, and then later repositioned at the positions shown in dotted line at 120' and 120".

Once the needle has been deployed along the length of rail 117, it is not necessary to withdraw and reinsert catheter 111 along a different one of the rails 117, as in the embodiment of FIG. 9. Instead, guide system 112 may be collapsed slightly from its fully expanded configuration, rotated a desired angle about its axis L, and then re-expanded to bring needle 120 into alignment with a different portion of the endocardial surface. This process may be repeated a desired number of times by the clinician, under fluoroscopic guidance, to deposit the bioactive agent in the myocardium with a predetermined pattern.

Figure 11A:
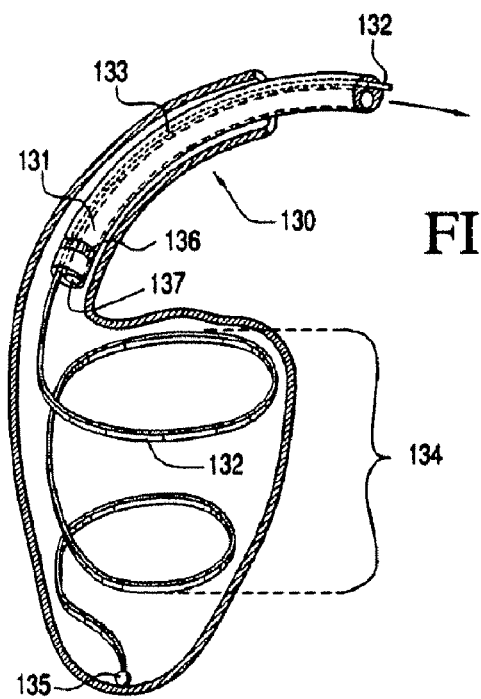
FIGS. 11A-11C show a further alternative rail system for use with the catheter of the present invention and a method of using same.
Figure 11C:
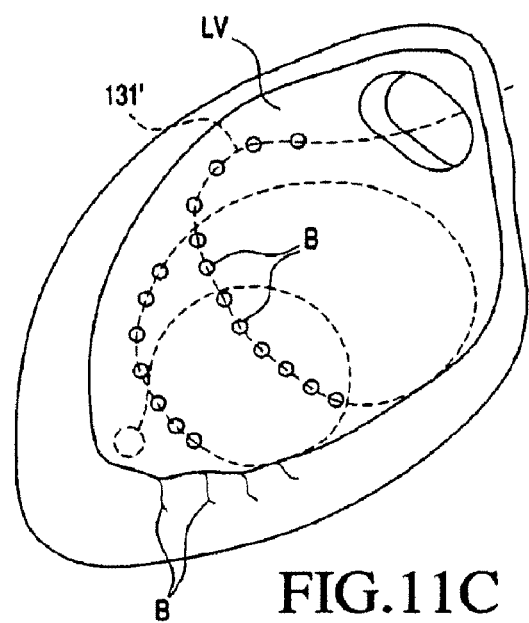
Figure 11B:
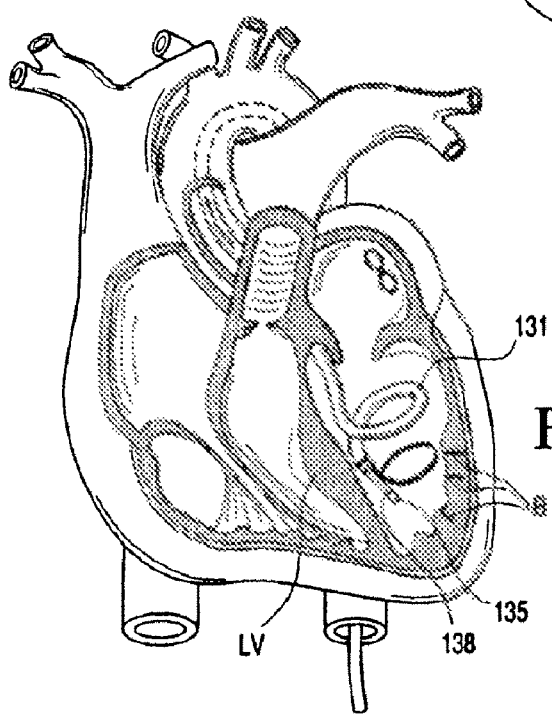

With respect to FIGS. 11A to 11C, another alternative configuration of a guide system suitable for use with the delivery system of the present invention is described. Delivery system 130 includes catheter 131, similar to that of FIGS. 4-6, and configured to be advanced along guide rail 132 similar to that described in U.S. Pat. No. 5,730,741 to Horzewski et al. Guide member 133 of catheter 131 comprises an internal lumen disposed within the interior of the catheter that enables the catheter to be translated along guide rail 132, although the external arrangement of the guide member, as shown in FIGS. 4-6, may be substituted.

Guide rail 132 includes portion 134 that expands to a helical configuration when released from a delivery sheath (not shown). Rail 132 preferably includes atraumatic bumper 135 at its distal end that engages the left ventricle near the apex. Catheter 131 preferably includes a radio-opaque marker 136 disposed near tip 137 that permits the clinician to locate the tip of the catheter as it is advanced along guide rail 132.

Operation of the delivery system 130 is described with respect to FIG. 11B, where guide rail 132 is shown deployed in the left ventricle. For example, guide rail may first be inserted, contracted within a sheath, via a femoral artery route into left ventricle LV. The sheath then is removed so that portion 134 of guide rail 132 expands into a helical configuration that contacts the endocardial surface.

Next, catheter 131 is advanced along the guide rail under fluoroscopic guidance until distal tip 137 of the catheter is located at a desired position adjacent to the endocardial surface. Needle 138 then is extended beyond the tip of catheter 131 to deposit bioactive agent B into the myocardium along the needle track, as described hereinabove with respect to the embodiments of FIGS. 4-6. Once the bioactive agent is deposited within the myocardium at the selected site, needle 138 is retracted into catheter 131, and the catheter is advanced or retracted along guide rail 132 to dispose distal tip 137 at a new location. The process is repeated until the bioactive agent B has been deposited at a plurality of sites as illustrated in FIG. 11C. Catheter 131 then is removed, and guide rail 132 may be re-sheathed to its collapsed configuration and removed, completing the procedure.

A further alternative configuration of a guide system suitable for use with the delivery system of the present invention is described with respect to FIGS. 12A-12D. Delivery system 140 includes catheter 141, similar to that of FIGS. 4-6, which has a flexible distal region that may be configured in-situ by advancing any of a plurality of interchangeable stylets, illustratively, stylets 142a (FIG. 12A), 142b (FIG. 12B) and 142c (FIG. 12C) within the device once it is located within the left ventricle. Guide member 143 of catheter 141 comprises internal lumen 144 disposed within the interior of the catheter that enables the catheter to be initially translated along a conventional guide wire, although the external arrangement of the guide member, as shown in FIGS. 4-6, also may be substituted. Once disposed in the left ventricle, the guide wire is withdrawn and a selected one of the stylets inserted.

Each stylet 142a-142c has a predetermined configuration that assists in urging catheter 141 against a selected portion of the endocardial surface. Each of stylets 142a-142c preferably includes atraumatic J-shaped termination 145 at its distal end that engages the left ventricle near the apex. Catheter 141 preferably includes radio-opaque marker 146 disposed near tip 147 that permits the clinician to locate the tip of the catheter as it is advanced along the stylet. In addition, each stylet may include spaced-apart radioopague markers, e.g., every 1 cm, so that the clinician can radiographically verify the injection locations by aligning marker 146 sequentially with the markings on the selected stylet.

Operation of the delivery system 140 is as follows. First, an atraumatic guidewire is placed in the left ventricle. Over this wire catheter 141 is advanced to the left ventricular apex. The guidewire is then removed and a stylet (for example 142a) is advanced into the catheter until it exits near the apex. The stylet will have a predetermined shape that will direct the catheter 141 into the target region of myocardium. Ridges in the catheter will also help direct delivery system 148 preferentially towards the endocardium. Second, catheter 141 is gradually retracted and multiple treatments are administered in this region at predetermined distances apart. Lastly, the catheter 141 is advanced back over the stylet into the left ventricular apex and stylet 142a is exchanged for another (for example 142b). The process is then repeated. Alternatively a selected stylet, e.g., stylet 142a, is inserted into the patient's left ventricle LV via a femoral artery route. The stylet may be constrained within a retractable sheath (not shown) that then is removed so that the stylet assumes a predetermined shape that contacts a portion of the endocardial surface.

Next, catheter 141 is advanced along the stylet under fluoroscopic guidance until distal tip 147 of the catheter is located at a desired position adjacent to the endocardial surface. Needle 148 then is extended beyond the tip of catheter 141 to deposit bioactive agent B into the myocardium along the needle track, as described hereinabove with respect to the embodiments of FIGS. 4-6. Once the bioactive agent is deposited within the myocardium at the selected site, needle 148 is retracted into catheter 141, and the catheter is advanced or retracted along stylet 142a to dispose distal tip 147 at a new location. The process is repeated until bioactive agent B has been deposited at a plurality of sites along the length of the stylet.

Figure 12A:
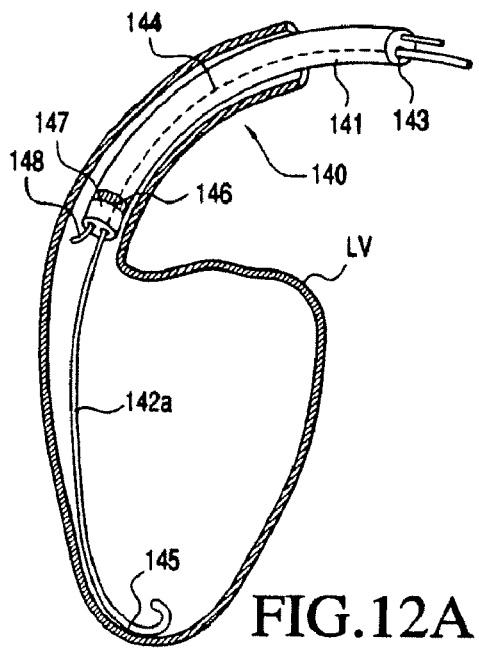
FIGS. 12A-12D show a stylet system for use with the catheter of the present invention and a method of using same.
Figure 12B:
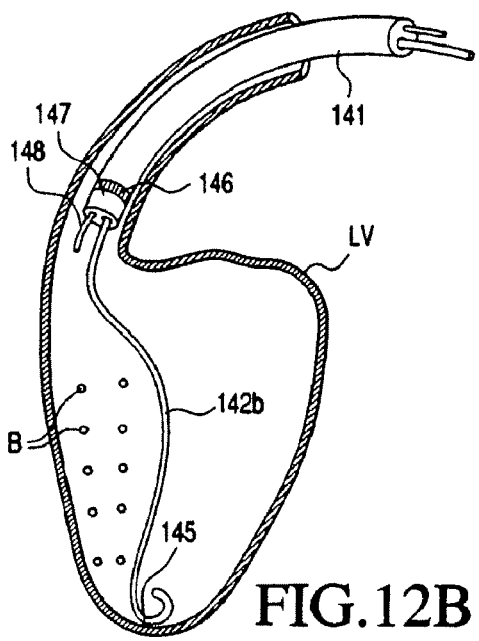
Figure 12C:
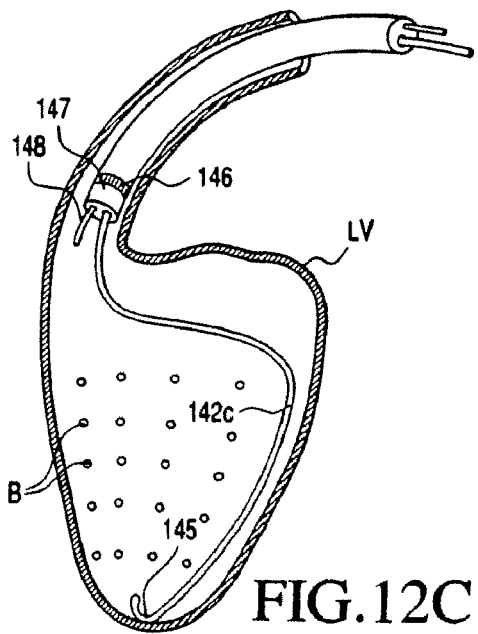

Catheter 141 is then fully advanced into the left ventricle, while stylet 142a is withdrawn from catheter 141, and stylet 142b, having a different preformed shape, is inserted into lumen 144 to urge catheter 141 against a different portion of the endocardial surface (FIG. 12B). Needle 148 then is extended to deposit bioactive agent B at locations along the length of the stylet. In addition, stylet 142b may be rotated through a predetermined angle relative to its longitudinal axis to reposition the catheter within the section of endocardial surface corresponding to the selected stylet, and additional needle tracks formed.

Figure 12D:
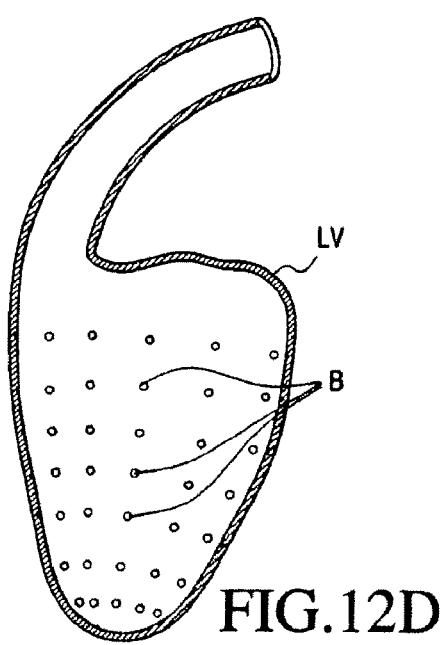

Stylet 142C then may be exchanged for stylet 142b, and the above process repeated to deposit the bioactive agent at additional locations within the myocardium. FIG. 12D illustrates the pattern of bioactive agent B seeded needle tracks that may be formed using delivery catheter 141 and stylets 142a-142c of the present invention. As will be apparent to one of skill in the art of medical devices, the stylets may be made in more or fewer predetermined shapes as required for the specific medical application and organ to be treated.

In addition to delivery of a bioactive agent via the endocardial surface, the present invention also contemplates delivery of a bioactive agent via an epicardial route. More specifically, the bioactive agent may be deposited in the myocardium using the inventive delivery catheters disposed along an access route via the coronary sinus and cardiac veins. FIG. 13 depicts the cardiac venous system of a typical human heart, which comprises coronary sinus CS that provides drainage for great cardiac vein GCV, middle cardiac vein MCV, and small cardiac vein SCV. Deoxygenated blood flowing into coronary sinus CS exits via coronary ostium O into the right atrium.

It is known in the art to access the epicardial surface via a coronary vein to provide transvenous retrograde myocardial perfusion, as described, for example, in U.S. Pat. No. 5,655,548 to Nelson et al. and to deliver drugs into the myocardium, as described in U.S. Pat. No. 6,159,196 to Ruiz. The present invention may advantageously employ this access route with the atraumatic injection techniques implemented by the methods and apparatus of the present invention.

Referring to FIG. 14, delivery system 150 includes catheter 152 having guide wire lumen 152 and needle lumen 153. Elongated needle 154, such as described above with respect to FIGS. 6 and 7, is translatably disposed in needle lumen 153. The proximal portion of needle 154 may be similar in construction to that of the embodiment of FIG. 6, and further includes radio-opaque marker 155 that is visible under fluoroscopic imaging. Distal portion 156 of needle 154 may be sufficiently flexible to bend through the curve imposed by needle lumen 153, so as to extend from the lateral surface of the catheter. Guide wire lumen 152 is configured to accept conventional guide wire 157, as depicted in FIG. 14.

In FIG. 15A, catheter 151 is shown disposed in coronary sinus CS on guide wire 157. This may be accomplished by first placing guide wire 157 via a femoral vein. Catheter 151 then is advanced along the guide wire until its distal end passes through the right atrium and coronary ostium into the coronary sinus. Once positioned in the coronary sinus CS or an adjoining coronary vein, needle 154 is extended from needle lumen into the myocardium, as depicted in FIG. 15B. Bioactive agent B, such as a suspension of stem cells, then is deposited in the needle track formed by needle 154.

Needle 154 then is retracted, and catheter 151 may be advanced further along guide wire 157 to deposit the bioactive agent along additional sites in the myocardium accessible via the coronary veins. While use of the coronary veins in this manner simplifies the delivery system by obviating the guide systems of FIGS. 6-9, epicardial access via the coronary veins will be limited to the sites accessible from those veins.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of depositing a bioactive agent into a tissue mass comprising native tissue, comprising:
    providing a catheter having a proximal end and a distal region and a lumen extending therebetween, an elongated member disposed within the lumen of the catheter, the elongated member having a proximal end, a tissue-piercing distal end, and a lumen extending therebetween, and an actuator for selectively extending and retracting the tissue-piercing distal end of the elongated member;
    disposing the distal region of the catheter adjacent to a tissue mass;
    operating the actuator to extend the elongated member into the tissue mass to form a needle track having a needle track entrance and a needle track distal region; and
    atraumatically delivering the bioactive agent into the needle track distal region via the lumen while retracting the elongated member from the tissue mass so that the native tissue fills in and closes the needle track entrance after the tissue-piercing distal end is removed from the needle track and without creating potential for leakage of the bioactive agent via the needle track entrance.

2. The method of claim 1 wherein delivering the bioactive agent into the needle track employs capillary action during retraction of the tissue-piercing distal end of the elongated member.

3. The method of claim 1 further comprising providing the bioactive agent to the lumen from a container and relieving negative pressure from within the container.

4. The method of claim 1 wherein the tissue-piercing distal end of the elongated member comprises means for creating a space adjacent to the distal end to receive the bioactive agent and delivering the bioactive agent into the needle track comprises delivering the bioactive agent into the space.

5. The method of claim 4 wherein the means for creating a space adjacent to the distal end comprises a wire disposed across the distal end, the method further comprising extending the wire to form the space.

6. The method of claim 1 wherein the catheter further comprises a guide system comprising at least one member configured to urge the catheter against an interior surface of a hollow organ and a guide member affixed to a distal region of the catheter, the method further comprising translating the guide member along the at least one member to dispose the distal region of the catheter adjacent to the tissue mass.

7. The method of claim 1 wherein the bioactive agent comprises stem cells.

8. The method of claim 1 wherein the bioactive agent comprises a drug.

9. The method of claim 1 wherein the tissue mass comprises an endocardial tissue mass.

10. The method of claim 1 wherein the tissue mass comprises a left ventricle.

11. The method of claim 1 wherein the tissue-piercing distal end comprises a needle.

12. The method of claim 1 wherein the actuator comprises a lever that translates the elongated member in proximal and distal directions.

13. The method of claim 12 wherein operating the actuator comprises depressing the lever.

14. The method of claim 1 further comprising a providing a guide system having at least one member configured to urge the catheter against an interior surface of a hollow organ, the catheter slidably engaged with the at least one member.

15. The method of claim 14 wherein the at least one member comprises a stylet having a predetermined deployed shape.

16. The method of claim 15 further comprising advancing the stylet into a left ventricle via a femoral artery route.

17. The method of claim 15 wherein the stylet comprises a radio-opaque marker.

18. The method of claim 17 further comprising disposing a distal region of the stylet adjacent to the tissue mass using fluoroscopic guidance.

19. The method of claim 1 wherein the catheter further comprises a radio-opaque marker disposed near the distal tip of the catheter.

20. The method of claim 19 wherein the disposing comprises disposing the distal region of the catheter adjacent to the tissue mass using fluoroscopic guidance.

* * * * *